(12) United States Patent
Vilsmeier (10) Patent No.: US 9,662,064 B2
(45) Date of Patent: May 30, 2017

(54) AUTOMATIC TREATMENT PLANNING METHOD USING RETROSPECTIVE PATIENT DATA

(71) Applicant: Brainlab AG, Feldkirchen (DE)

(72) Inventor: Stefan Vilsmeier, Munich (DE)

(73) Assignee: Brainlab AG, Munich (DE)

( * ) Notice: Subject to any disclaimer, the term of this patent is extended or adjusted under 35 U.S.C. 154(b) by 91 days.

(21) Appl. No.: 13/632,499

(22) Filed: Oct. 1, 2012

(65) Prior Publication Data
US 2013/0085779 A1    Apr. 4, 2013

Related U.S. Application Data

(60) Provisional application No. 61/542,161, filed on Oct. 1, 2011.

(30) Foreign Application Priority Data

Oct. 1, 2011   (EP) ..................................... 11183650

(51) Int. Cl.
*A61B 5/00*   (2006.01)
*G06F 19/00*   (2011.01)

(52) U.S. Cl.
CPC ........ *A61B 5/4842* (2013.01); *G06F 19/3443* (2013.01); *G06F 19/321* (2013.01)

(58) Field of Classification Search
CPC .............. G06F 19/322; G06F 19/3431; G06F 19/3418; G06Q 50/24; G06Q 50/22
USPC ..................................................... 705/2, 3, 4
See application file for complete search history.

(56) References Cited

U.S. PATENT DOCUMENTS

| | | | |
|---|---|---|---|
| 2005/0049477 A1* | 3/2005 | Fu | A61N 5/1049 600/407 |
| 2006/0120583 A1* | 6/2006 | Dewaele | 382/128 |
| 2009/0290772 A1* | 11/2009 | Avinash | G06F 19/3487 382/130 |
| 2010/0125462 A1* | 5/2010 | Aggarwal | G06Q 50/24 705/3 |
| 2010/0191541 A1* | 7/2010 | Prokoski | A61B 5/0064 705/2 |

(Continued)

FOREIGN PATENT DOCUMENTS

| | | | | |
|---|---|---|---|---|
| WO | WO 0100083 A1 * | 1/2001 | ......... | G06F 19/3437 |
| WO | 2011068475 A1 | 6/2011 | | |

OTHER PUBLICATIONS

European Search Report, 12186747.7-1951/2575067, Aug. 7, 2015, pp. 8, The Hague, European Patent Office, Munich Germany.

(Continued)

*Primary Examiner* — Elaine Gort
*Assistant Examiner* — John Go
(74) *Attorney, Agent, or Firm* — Tucker Ellis LLP (57) ABSTRACT

A data processing method for planning a medical treatment comprising following steps performed by a computer:
  acquiring reference patient data describing medical information on at least one reference patient including information on progression of the medical constitution of the at least one reference patient;
  acquiring current patient data describing medical information on a current patient;
  determining information on the progression of the medical constitution of the current patient based on the reference patient data and the current patient data.

14 Claims, 3 Drawing Sheets

(56) References Cited

U.S. PATENT DOCUMENTS

| | | | |
|---|---|---|---|
| 2010/0195890 A1* | 8/2010 | Berlinger | A61B 6/032 382/131 |
| 2010/0228340 A1* | 9/2010 | Erbel | A61F 2/88 623/1.18 |
| 2011/0046979 A1 | 2/2011 | Tulipano et al. | |

OTHER PUBLICATIONS

Zacharaki,E.I. et al., "Orbit:A Multiresolution Framework for Deformable Registration of Brain Tumor Images", IEEE Transactions on Medical Imaging, IEEE service center, Piscataway, NJ, US, vol. 27 No. 8, Aug. 1, 2008, pp. 1003-1017, XP011224706, ISSN: 0278-0062, D01: 10.1109/TMI.2008.916954 *abstract*.

* cited by examiner

AUTOMATIC TREATMENT PLANNING METHOD USING RETROSPECTIVE PATIENT DATA

RELATED APPLICATION DATA

This application claims priority of the U.S. Provisional Application No. 61/542,161 filed on Oct. 1, 2011, which is incorporated herein by reference in its entirety.

The present invention is directed to a method, in particular a data processing method for planning a medical treatment as defined by the independent claim.

In radiation oncology preventative radiation is used to reduce the risk of tumor growth such as for metastases in the brain. This is controversial due to the effect on the cognitive function of the brain and is reviled by treating metastases as they occur.

A problem to be solved by the invention is to provide an automatic treatment planning.

This problem is solved by the subject-matter of the independent claim. Advantages, advantageous features, advantageous embodiment and advantageous aspects of the present invention are disclosed in the following and are contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Preferably, the inventive method is at least partly executed by a computer. That is, all steps or just some of the steps (i.e. less than a total number of steps) of the inventive method may be executed by a computer.

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. However, some of the changes in the anatomical structure, in particular the pathological changes in the structures (tissue), may not be detectable and in particular may not be visible in the images generated by the imaging methods. A tumour for example represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. The MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernable in the image generated by the imaging method. In addition to these tumours, referred to as "enhancing" tumours, it is thought that approximately 10% of brain tumours are not discernable on a scan and are in particular not visible to a user looking at the images generated by the imaging method.

In this application, the term "image morphing" is also used as an alternative to the term "image fusion", but with the same meaning.

Elastic fusion transformations (e.g. image fusion transformation) are in particular designed to enable a seamless transition from one data set (e.g. first data set, e.g. first image) to another data set (e.g. second data set, e.g. second image). The transformation is in particular designed such that one of the first and second data sets (images) is deformed, in particular in such a way that corresponding structures (in particular, corresponding image elements) are arranged at the same position as in the other of the first and second images. The deformed (transformed) image which is transformed from one of the first and second images is in particular as similar as possible to the other of the first and second images. Preferably, (numerical) optimisation algorithms are applied in order to find the transformation which results in an optimum degree of similarity. The degree of similarity is preferably measured by way of a measure of similarity (also referred to in the following as a "similarity measure"). The parameters of the optimisation algorithm are in particular vectors of a deformation field F. These vectors are determined by the optimisation algorithm which results in an optimum degree of similarity. Thus, the optimum degree of similarity represents a condition, in particular a constraint, for the optimisation algorithm. The bases of the vectors lie in particular at voxel positions of one of the first and second images which is to be transformed, and the tips of the vectors lie at the corresponding voxel positions in the transformed image. A plurality of these vectors are preferably provided, for instance more than twenty or a hundred or a thousand or ten thousand, etc. Preferably, there are (other) constraints on the transformation (deformation), in particular in order to avoid pathological deformations (for instance, all the voxels being shifted to the same position by the transformation). The constraints include in particular the constraint that the transformation is regular, which in particular means that a Jacobian determinant calculated from a matrix of the deformation field (in particular, the vector field) is larger than zero. The constraints include in particular the constraint that the transformed (deformed) image is not self-intersecting and in particular that the transformed (deformed) image does not comprise faults and/or ruptures. The constraints include in particular the constraint that if a regular grid is transformed simultaneously with the image and in a corresponding manner, the grid is not allowed to interfold at any of its locations. The optimising problem is in particular solved iteratively, in particular by means of an optimisation algorithm which is in particular a first-order optimisation algorithm, in particular a gradient descent algorithm. Other examples of optimisation algorithms include optimisation algorithms which do not use derivations such as the downhill simplex algorithm or algorithms which use higher-order derivatives such as Newton-like algorithms. The optimisation algorithm preferably performs a local optimisation. If there are a plurality of local optima, global algorithms such as simulated annealing or genetic algorithms can be used. In the case of linear optimisation problems, the simplex method can for instance be used.

In the steps of the optimisation algorithms, the voxels are in particular shifted by a magnitude in a direction such that the degree of similarity is increased. This magnitude is preferably less than a predefined limit, for instance less than $\frac{1}{10}$ or $\frac{1}{100}$ or $\frac{1}{1000}$ of the diameter of the image, and in particular about equal to or less than the distance between neighbouring voxels. Due in particular to a high number of (iteration) steps, large deformations can be implemented.

The determined elastic fusion transformation can be in particular used to determine a degree of similarity (similarity measure also referred to as "measure of similarity") between the first and second data set (first and second image). To this end, the deviation of the elastic fusion transformation and an identity transformation is determined. The degree of deviations can be for instance calculated by determining the difference between the determinant of the elastic fusion transformation and the identity transformation. The higher the deviation is the less is the similarity. Thus, the degree of deviation can be used to determine a measure of similarity.

A measure of similarity can in particular be determined on the basis of a determined correlation between the first and second data set.

The inventive method is a data processing method and constitutes a method for planning a medical treatment and for determining a treatment plan. A treatment plan preferably describes a medical treatment to be carried out on a patient. In particular a treatment plan comprises information about pharmaceuticals to be given to the patient, for example about the type of pharmaceuticals and the dose in which they are to be applied. In case the medical treatment to be carried out comprises treatment by radiotherapy, a treatment plan in particular comprises information about the points in time and/or the time intervals at which radiotherapy sessions are to be conducted on the patient. In the case of radiotherapy treatment, the term dose refers to a radiation dose caused by radiation within particular treatment radiation. Besides that, a radiotherapy treatment plan in particular comprises information about the kind of a dose (more particularly, the energy and time length of radiation) of radiation to be applied. Furthermore, radiotherapy treatment plan may comprise information about the location of the target region and in the patient's body and the kind of disease from which the patient is suffering (such as the kind of tumor to be radiated). In particular, a treatment plan for radiotherapy comprises information about the relative position between the target region and an arrangement of treatment beams. In general, a treatment plan may also comprise information about the anatomic or physiology of the patient, such as information about his height and weight, his gender, age and vital parameters (such as blood pressure, breathing frequency and heart rate). A radiotherapy treatment plan in particular comprises information about the treatment beam or treatment beams to be used, in particular by the arrangement of treatment beams. More particularly, a radiotherapy treatment plan comprises information about the positional arrangement of the arrangement of treatment beams, advantageously the position of the positional arrangement relative to the patient's body (in particular, relative to the target region, relative to healthy tissue and relative to critical structures). Preferably, the position of each beam line relative to the patient's body (or the aforementioned parts of the patient's body) is described by information contained in the treatment plan. Information describing the geometric relationship (for example the position of the positional arrangement relative to the patient's body and the positional arrangement itself) is in the framework of this disclosure also called patient-beam-relationship information.

According to the present invention, reference patient data is acquired describing medical information on at least one reference patient including information on progression of the medical constitution of the at least one reference patient. Preferably, reference patient data comprising reference patient information about the reference patient's body is acquired. The reference patient information comprises categories of information selected at least from the above-described categories of information which may be contained in the current patient information. Preferably, the reference patient data comprises information, preferably image information, about the geometry of at least part of the reference patient's body.

Preferably, the reference patient data comprises information, in particular image information, about the geometry of at least part of the reference patient's body. Preferably, the reference patient data comprises reference target region data comprising reference target region information about a reference target region in the reference patient body. The reference target region describes categories of information in analogy to those described by the current target region information, however with regard to the reference patient body if applicable.

According to the present invention, current patient data is acquired describing medical information on a current patient. Preferably, the current patient data contains similar information as reference patient data, particularly about a patient, preferably about a patient's body or body geometry. Preferably, current patient information contains image data taken from a current patient.

According to the present invention, information on the progression of the medical constitution of the current patient is determined based on the reference patient data and the current patient data.

Preferably, acquiring reference patient data comprises acquiring patient data of a plurality of patients. According to the present invention, reference patient data of any number of reference patients can be acquired.

According to a further preferred embodiment, acquiring reference patient data comprises acquiring patient data of at least one patient at different times. This means that a plurality of the same type of information is acquired from the same patient or the same patients, wherein a certain time period lies between the points in time at which reference patient data is acquired. In other words, a plurality of the same type of information is acquired in sequence, wherein a predetermined period of time lies between the points in time at which reference patient data is acquired. Patient data can be acquired by carrying out an examination on the patient. Preferably, at least two examinations are carried out on the patient or the patients, wherein the number of examinations is not limited according to the present invention. However, a sufficient number of examinations of a patient or a plurality of patients should be carried out in order to allow examination of a progression of the medical constitution of one or more reference patients.

Preferably, the same examination is carried out several times on the same patient. More preferably, the same examination is carried out on a plurality of reference patients several times.

Preferably, the patient data is taken from a data base providing patient data. In other words, patient data can be acquired and stored afterwards in a data base for further use. When patient data is needed at a later point in time, it can be taken from the data base.

Preferably, information on the progression of the medical constitution of the at least one reference patient includes a sequence of medical constitution data of the at least one reference patient. This means that information on the progression of the medical constitution for each reference patient includes medical constitution data acquired by means of a plurality of examinations as described above which have been carried out at different points in time so as to allow examination of the progression of the medical constitution of the respective patient/patients.

Preferably, the sequence of medical constitution data comprises a sequence of image data of the at least one reference patient. It is understood that a predetermined plurality of image data can be acquired subsequently of at least one patient.

It is to be said that acquiring patient data means that data of a target region of a patient can be acquired, for example a region or a point of interest or a region or a point to be treated, for example the brain or part of the brain.

Preferably, additional data on the progression of the medical constitution of the at least one reference patient is generated based on the sequence of medical constitution data, particularly information, from a chronological point of view lying between the acquired medical constitution data. In other words, "artificial" data containing information on the progression of the medical constitution is generated from existing medical constitution data which has been acquired by means of examinations. For example, when a sequence of image data of a patient has been acquired by examination at subsequent points in time, further image data can be generated, particularly computed (for example by interpolation) form the existing image data in order to generate image data which, from a chronological point of view, lies between existing image data. By means of this, a smoother transition between the image data can be obtained for further use.

Preferably, acquiring current patient data comprises acquiring patient data of a patient at least once, particularly by carrying out at least one examination of the current patient. Although one single examination of the current patient allows determination of information of the progression of the medical constitution of the current patient based on the reference patient data and the current patient data, it is preferred to acquire current patient data by means of a plurality of examinations of the current patient which already allows a certain determination on the progression of the medical constitution of the current patient based on the current patient data only.

Preferably, the examination carried out on the current patient is the same type of examination as carried out on a reference patient or a plurality of reference patients. It is understood that carrying out the same examination on the current patient as already carried out on at least one reference patient enhances predictability on the progression of the medical constitution of the current patient.

Preferably, the step of acquiring reference patient data comprises receiving the reference patient data. Reference patient data can be provided by any suitable means of including storing devices, examination devices, manual input of a surgeon etc.

Moreover, the step of acquiring reference patient data preferably comprises:
- acquiring criteria data describing criteria for comparing pool patient data to current patient data, the reference patient data comprising patient data of a plurality of patients
- determining the reference patient data form a plurality of reference patients, particularly form a data base providing acquired patient data of a plurality of patients by selecting a set of the patient's data based on the criteria for comparing patient data to current patient data. In other words, available pool patient data is selected using certain criteria data so as to use only suitable reference patient data for determining information on the progression of the medical constitution of the current patient based on the pool patient data and the current patient data.

Preferably, criteria data comprises generic medical data, for example age, gender, blood group, height, weight, etc.

Selecting reference patient data enhances predictability of the medical constitution of the current patient, since the same conditions underlie the medical constitution of the current patient as well as of the reference patient/patients.

Preferably, the criteria comprise predetermined criteria and/or criteria determined based on the candidate patient data. In particular, the criteria are flexible adapted in dependence on the candidate patient data in order to find the best suitable criteria which are applicable for the assessment of the treatment plan for the present patient. For instance, data describing a table (which links patient data with the criteria) are provided. Depending on the patient data, those criteria are selected which are linked in accordance with the table. For instance, different criteria can be applied in dependence on the status of progression of a tumour. The status of progression is described by the candidate patient data. The criteria may for instance also depend on the age of the patient. For instance, criteria describing a dose limit for parts of the body may depend on age of the patient and/or progression of the tumour. The criteria can be based on tumour grades, ICD-9 classification, Simpson grade, oxygenation of tumour, degree of metastasis of tumour, blood count values, tumour indicator values, like PSA value.

Preferably, criteria data describes a requirement according to which medical information at the time of a particular status of progression of the medical constitution is included in the patient data of a patient. Preferably, the criteria is that the particular status of progression corresponds at least partly to the status of progression of the medical constitution of the current patient.

Preferably, determining information of the progression of the medical constitution of the current patient comprises determining the statistical probability of at least one progression scenario of the medical constitution of the current patient based on the reference patient data and the current patient data.

Preferably, at least one progression scenario of the medical constitution of the current patient is a future progression scenario. In other words, the type and probability of the progression of the medical status of the current patient is predicted to a certain degree based on reference patient data and current patient data.

Preferably, determining reference patient data comprises superimposing reference patient data, particularly reference patient image data. This means that a "reference patient-model" can be generated for further use. By means of this, analysis-time can be reduced.

Preferably, elastic fusion is used to cross-reference data of a reference patient with data of another reference patient, particularly to cross-reference anatomical data of a reference patient with anatomical data of another reference patient, particularly before superimposing reference patient data, particularly reference patient image data. In order to "generate" a certain conformity of a plurality of reference patients, elastic fusion as described further above is used.

Preferably, determining the reference patient data comprises determining similarity of current patient data and reference patient data. This means that the current patient is compared with at least one reference patient in order to select reference patient data which is suitable for determining information on the progression of the medical constitution of the current patient, particularly for determining the statistical probability of at least one progression scenario of the medical constitution of the current patient based on the reference patient data and the current patient data.

Preferably, determining similarity of current patient data and reference patient data comprises considering similarity of the status of progression of the medical constitution of the current patient and a reference patient.

Preferably, elastic fusion as described further above is used to cross-reference current patient data with reference patient data, particularly to cross-reference anatomical current patient data with anatomical reference patient data, particularly for determining similarity of current patient data and reference patient data. Preferably, a similarity threshold, for example a minimum value and/ore a maximum value is set for similarity of current patient data and reference patient data.

Preferably, at least one progression scenario is based on reference patient data fulfilling criteria concerning similarity of current patient data and reference patient data, particularly lying within the similarity threshold.

Preferably, data subtraction, particularly 3D data subtraction is used to determine the degree of similarity. More preferably, image data subtraction is used to determine the degree of similarity.

Preferably, information on the progression of the medical constitution of the current patient, particularly the statistical probability of at least one progression scenario of the medical constitution of the current patient is provided, particularly displayed to a person.

Preferably, treatment data is acquired describing a plurality of potential treatments for the determined progression of the medical constitution of the current patient, particularly the statistical probability of at least one progression scenario of the medical constitution of the current patient.

Preferably, treatment criteria data is acquired and at least one suitable treatment is selected based on treatment criteria data, and the at least one selected treatment is provided, particularly displayed to a person.

Preferably, a treatment decision is made based on criteria data acquired for selecting at least one appropriate treatment, preferably the most appropriate treatment.

Preferably, a medical treatment is a radiation therapy treatment. Preferably, the progression analyzed is the development of metastasis in the human body, particularly of metastasis in the human brain or part of the human brain.

Preferably, the order and/or location at which metastasis for the current patient is compared to the order and/or location of metastasis for the at least one reference patient.

Preferably, cloud technology is used for acquiring patient data. Preferably, at least one cloud based server is used for determining information on the progression of the medical constitution of the current patient.

The invention also relates to a program, when running on a computer, causes the computer perform one or more or all of the method steps described herein and/or to a program storage medium on which the program is stored/in particular in a non-translatory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein.

Preferably, the computer on which the aforementioned program is running is or comprises a cloud server.

In the following, example embodiments of the present invention are described within reference to the figures, which are merely to be regarded as examples of the invention without limiting the invention to these specific embodiments, wherein.

It is to be noted that, in the following the present invention is described by means of an example for the inventive data processing method which is concerned with the determination, in particular prediction of a progression of the medical constitution of a current patient. In this context, a brain is just an example for an anatomical structure of the current patient or the reference patient. Moreover, a tumor or metastasis is just an example for a pathological structure. Further examples for anatomical structures are: lunge, liver, skin or any other organ of a patient.

Figure 1:
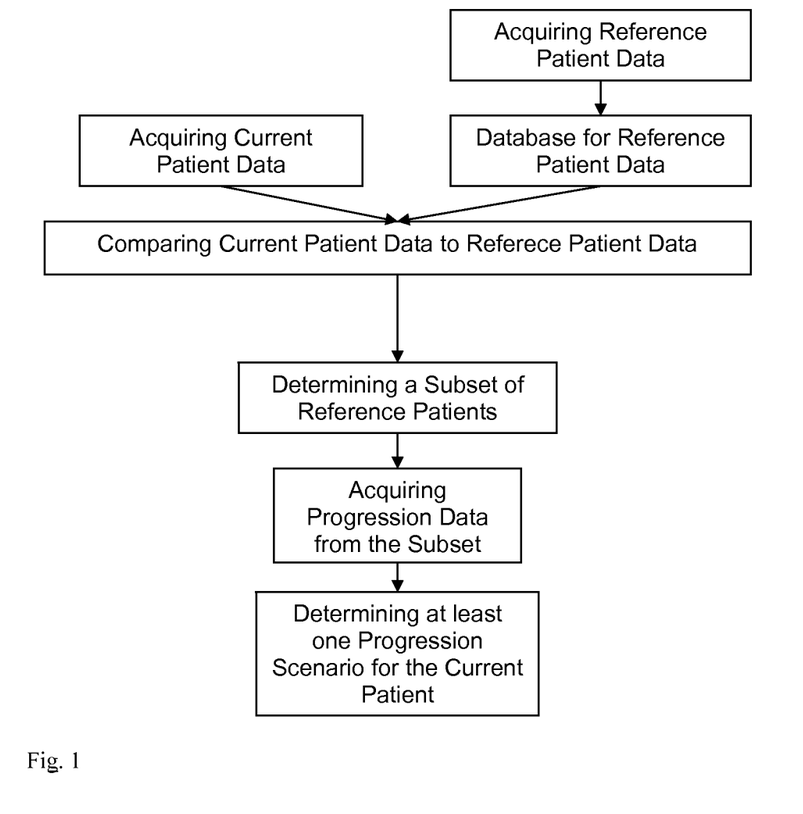
FIG. 1: shows a flow diagram as an example of the inventive automatic treatment planning method.

As shown in FIG. 1, patient data of a plurality of patients is acquired, for example by oncological examination. For example, a plurality of images can be taken from the brain of the patients which suffer from brain tumor which develops metastasis in other regions. By a taking a plurality of subsequent images, the growth of the tumor and the development of metastasis can be observed over time.

Preferably, the acquired pool patient data is then stored in a database for patient data, which allows retrospective analysis of patients and their history of developing metastasis.

Preferably, criteria data is also acquired which allows to select a certain amount of reference patients from the pool patients stored in a database.

Patient data of a current patient which suffers from a brain tumor and undergone the same examination as undertaken for at least some reference patients is then acquired which allows comparisment of the current patient data to the reference patient data, thereby using cloud technology. This means that reference patient data is stored on ore or several cloud servers which provide data to a client computer which is fed with current patient data, which can by the way also be stored on a database on a cloud server, and reference patient data so as to compare current patient data to reference patient data.

Based on the pool patient data, the criteria data and the current patient data, a subset of reference patients is determined.

From the subset of reference patients, progression data is acquired which describes tumor growth and/or development of metastasis for the reference patients.

Based on this progression data, a statistical conclusion can be drawn for the current patient with a similar medical constitution as the reference patients from the subset concerning tumor growth and/or development of metastasis in the future.

Figure 2:
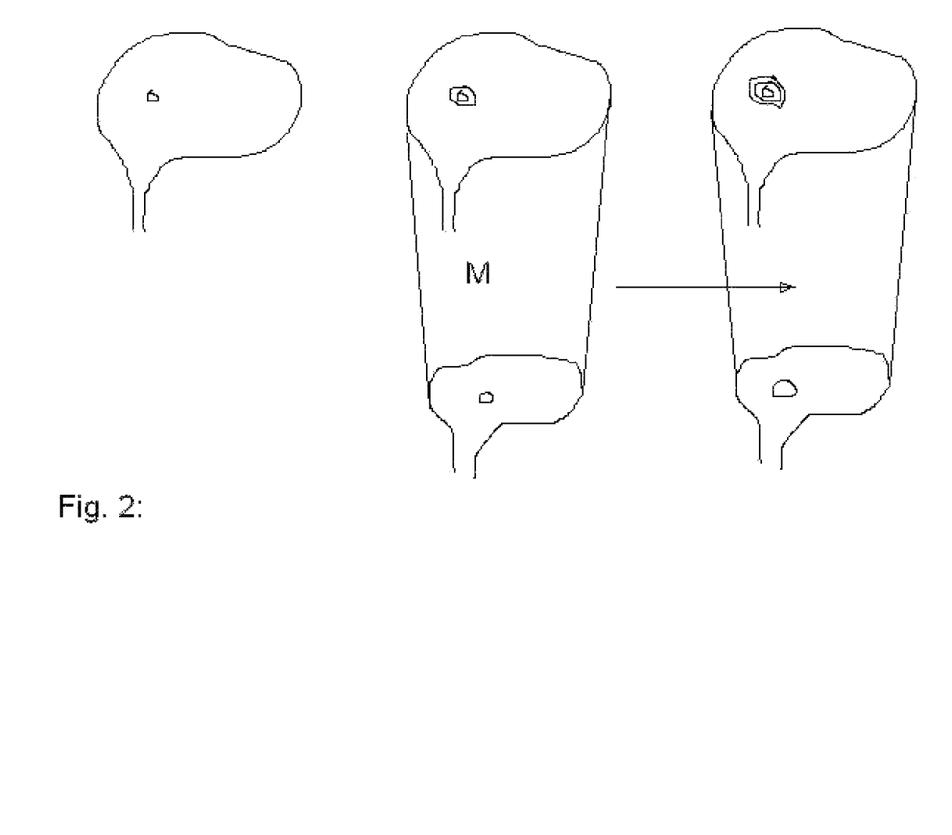
FIG. 2: shows applying of elastic fusion in order to predict tumor growth in a brain of a current patient.

FIG. 2 shows a brain of a reference patient or, more particular an "average" reference patient brain derived from data of a plurality of brains of a plurality of reference patients (e.g. by performing an arithmetical average mode average or mean average). Going from left to right of the sequence of reference patient brain data, it can be seen that the size of a tumor in the brain increases over time.

Having data of a current patients brain which is, for example smaller than the reference patients brain, a transformation matrix can be derived from the reference patients brain data and the current patients brain data. The transformation matrix describes in particular an elastic fusion. For determining the transformation, in particular the pathological parts described in the reference image and the current image are disregarded.

If tumor growth in the current patients brain is to be predicted for the future, the transformation matrix applied to future reference patients brain data (which describe a later image) can be used to predict a future image which describes the future size of the tumor in the current patients brain at a future time.

The time difference between the future time and the current time is the progression time difference. The current patient data describe a situation of the medical condition at the current time. The transformation matrix applied to the later image (or average later image which represents a statistical image) is preferably applied to the complete anatomical structure which includes the pathological structure so that also the pathological structure (in particular the statistical distribution thereof) is transformed.

The statistical image is in particular achieved by averaging or superimposing reference images which describe reference patients which are in the same stage of progression (of a decease, e.g. tumor progression). Before averaging or superimposing, the reference images can be adapted to each other or to a standard reference image by elastic fusion.

Figure 3:
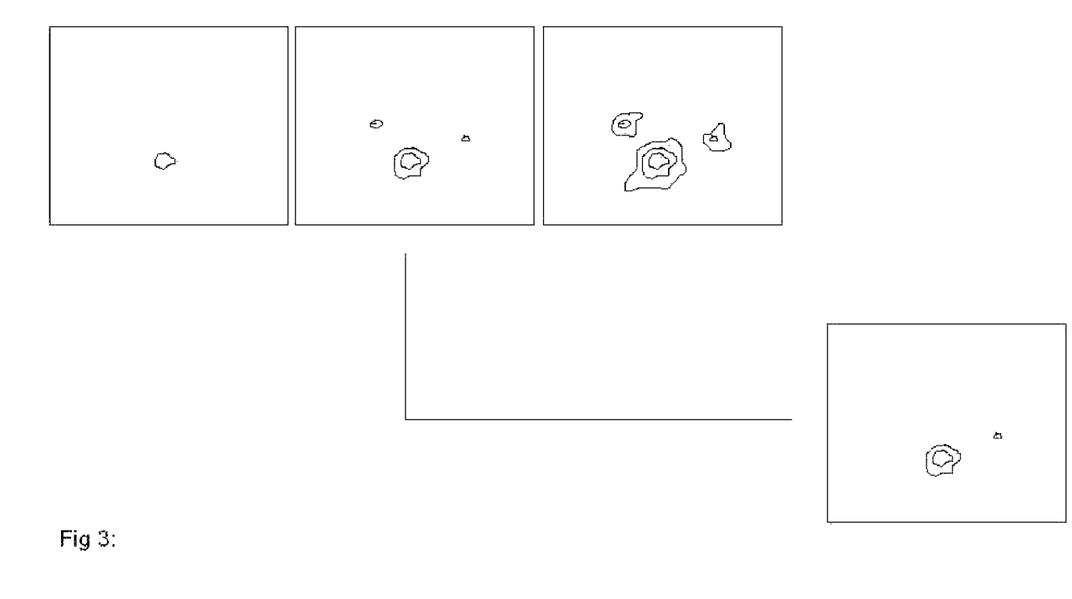
FIG. 3: shows a comparison of a sequence over time of reference patient image data to current patient image data.

As can be seen in FIG. 3, a sequence over time of preferably averaged reference patient image data showing tumor and metastasis growth is compared with current patient data so as to determine the status of progression of the medical constitution of the current patient compared with the reference patient. To this end, the most similar image in the sequence is selected to the selected image, a reference time is assigned. The predicted progression of the future time is reflected by the later reference image to which a later time is assigned. The time difference between the later image and the reference time is preferably at least approximately similar to the progression time difference. Thus, the later reference image is preferably determined based on the progression time difference, the reference time and the later time. The average of the reference images reflects a statistical probability.

In other words, the present invention can be described as follows:

A database derived from retrospective analysis of patients and their history of developing metastasis is used to determine the probability of growth, so that, for example, radiation can be delivered in areas of the brain above a certain statistical probability of developing metastasis prior to the next follow-up scan. The inventive method for planning medical treatments is based on the following steps:

Creating a database from multiple patients with multiple diagnostic examinations each, suitable to determine the progression of the medical condition of each patient, comparing a new patient to be treated with at least one diagnostic examination to the patients in the database using a plurality of criteria, using a subset of patients resulting from the comparison to calculate the statistical probability of one ore multiple progression scenarios for the new patient. Afterwards, a treatment decision can be made resulting from this statistical probability. In one preferred embodiment, the medical treatment is a radiation therapy treatment, wherein the progression analyzed is the development of metastasis.

Moreover, the order and location at which metastasis for the new patient occurred are compared to the order and location of metastasis for patients from the database. In order to determine the degree of similarity, 3D subtraction of data is used.

For cross-referencing the anatomy of various patients in a database relative to each other and relative to the new patient, elastic fusion is used. Moreover, the database uses cloud technology for easy access and the calculation may use cloud based servers for scalable calculation power to reduce the analysis time.

In the following part of the present specification, numbered examples are listed which are directed to advantageous embodiments. Said embodiments may represent separate or independent inventions. The embodiments and the features as listed may, separately or in groups, be combined in any manner to form embodiments belonging to the present disclosure.

Numbered examples:

1. A data processing method for planning a medical treatment comprising following steps performed by a computer:
    acquiring reference patient data describing medical information on at least one reference patient including information on progression of the medical constitution of the at least one reference patient;
    acquiring current patient data describing medical information on a current patient;
    determining information on the progression of the medical constitution of the current patient based on the reference patient data and the current patient data.
2. The method according to the preceding example, wherein the reference patient data comprises acquiring patient data of at least one patient at different times, particularly generated by carrying out at least two examinations of at least one reference patient at different times.

3. The method according to one of the preceding examples, wherein the same type of examination is carried out several times.

4. The method according to one of the preceding examples, wherein information on the progression of the medical constitution of the at least one reference patient includes a sequence of medical constitution data of the at least one reference patient.

5. The method according to one of the preceding examples, wherein the sequence of medical constitution data comprises a sequence of image data of the at least one reference patient.

6. The method according to one of the preceding examples, wherein additional data on the progression of the medical constitution of the at least one reference patient is generated based on the sequence of medical constitution data, particularly information, from a chronological point of view, lying between the acquired medical constitution data.

7. The method according to one of the preceding examples, wherein acquiring current patient data comprises acquiring patient data of a patient at least once, particularly by carrying out at least one examination of the current patient.

8. The method according to one of the preceding examples, wherein the examination carried out on the current patient is the same type of examination as carried out on a reference patient.

9. The method according to one of the preceding examples, wherein the step of acquiring reference patient data comprises receiving the reference patient data.

10. The method according to one of the preceding examples, wherein the step of acquiring reference patient data comprises:
    acquiring criteria data describing criteria for comparing pool patient data to current patient data, the pool patient data comprising patient data of a plurality of patients;
    determining the reference patient data of a plurality of reference patients, by selecting a set of the pool patient data, based on the criteria for comparing the pool patient data to the current patient data, and based on the current patient data and the pool patient data.

11. The method according to one of the preceding examples, wherein determining the reference patient data comprises determining similarity of current patient data and pool patient data.

12. The method according to one of the preceding examples, wherein determining the similarity of current patient data and pool patient data comprises considering similarity of the status of progression of the medical constitution of the current patient and a pool patient.

13. The method according to one of the preceding examples, wherein elastic fusion is used to cross-reference current patient data with pool patient data, particularly to cross-reference anatomical current patient data with anatomical pool patient data, particularly for determining similarity of current patient data and pool patient data.

14. The method according to one of the preceding examples, wherein a similarity threshold is set for similarity of current patient data and pool patient data.

15. The method according to one of the preceding examples, wherein at least one progression scenario is based on reference patient data fulfilling criteria concerning similarity of current patient data and reference patient data, particularly lying within the similarity threshold.

16. The method according to one of the preceding examples, wherein data subtraction, particularly 3D data subtraction is used to determine the degree of similarity.

17. The method according to one of the preceding examples, wherein image data subtraction is used to determine the degree of similarity.

18. The method according to one of the preceding examples, wherein reference patient data is taken from a database providing the acquired pool patient data.

19. The method according to one of the preceding examples, wherein criteria data comprises at least one of generic medical data, for example age, gender, blood group etc.

20. The method according to one of the preceding examples, wherein criteria data comprises at least one of tumor grades, ICD-9 classification, Simpson grade, oxygenation of tumor, degree of metastasis of tumor, blood count value tumor indicator value, like PSA value etc.

21. The method according to one of the preceding examples, wherein criteria data describes a requirement according to which medical information at the time of a particular status of progression of the medical constitution is included in the pool patient data of a patient.

22. The method according to one of the preceding examples, wherein the criteria is that the particular status of progression corresponds at least partly to the status of progression of the medical constitution of the current patient.

23. The method according to one of the preceding examples, wherein determining information on the progression of the medical constitution of the current patient comprises determining the statistical probability of at least one progression scenario of the medical constitution of the current patient based on the reference patient data and the current patient data.

24. The method according to one of the preceding examples, wherein at least one progression scenario of the medical constitution of the current patient is a future progression scenario.

25. The method according to one of the preceding examples, wherein determining the statistical probability comprises combining reference patient data of different reference patients, particularly combining reference patient image data.

26. The method according to one of the preceding examples, wherein elastic fusion is used to cross-reference data of a reference patient with data of another reference patient, particularly to cross-reference anatomical data of a reference patient with anatomical data of another reference patient, particularly before superimposing reference patient data, particularly reference patient image data.

27. The method according to one of the preceding examples, wherein images are 2D images or 3D images.

28. The method according to one of the preceding examples, wherein elastic fusion transformations are determined which perform a transformation between the reference images and the current image 29. The method according to one of the preceding examples, wherein information on the progression is determined based on elastic fusion performed between at least one reference image of the reference patient data and a current image of the current patient data.

30. The method according to one of the preceding examples, wherein the elastic fusion generates adapted reference images which have in particular a higher degree of similarity with respect to the current image.

31. The method according to one of the preceding examples, wherein the current patient data includes information on the status of progression of medical constitution of current patient assigned to current images of the current patient.

32. The method according to one of the preceding examples, wherein the reference data describe links between the status of progression and the reference images, so that the references images progression statuses are respectively defined for the reference images.

33. The method according to one of the preceding examples, wherein those ones of the reference images, referred to as suitable images, are selected for determining the information on the progression of the medical constitution of the current patient which are linked to the same or at least most similar status of progression as the status of progression linked to the current image and/or those ones of the reference images are used for determining the elastic fusion.

34. The method according to one of the preceding examples, wherein the elastic fusion is determined based in particular only on a healthy part of the anatomical structure described by the suitable images and a healthy part of the anatomical structure described by the current image.

35. The method according to one of the preceding examples, wherein a statistical probability of a progression is determined based on a plurality of individual reference images (later images), which individual reference images (later images) relate to a later stage of progression, wherein the individual reference images are (preferably) adapted reference images determined by elastic fusion or are not-adapted reference images to which the elastic fusion has not been applied.

36. The method according to the preceding example, wherein time difference data is acquired defining the progression time difference between present time and future time for which the progression is to be predicted.

37. The method according to the preceding example, wherein the individual reference images (later images) which relate to the later state of progression are determined by selecting those reference images of the different reference patient, which have at least approximately a time difference with respect to a time assigned the corresponding suitable image which time difference corresponds to the progression time difference (so that the selected individual reference images (later images) reflect the status of progression of the reference patients in accordance with an elapsed progression time difference wherein the progression time difference is added to a starting time at which the status of progression is described by the suitable images respectively for the respective reference patients).

38. The method according to one of the preceding examples, wherein if the individual reference images (later images) are determined based on not-adapted reference images, then the determined elastic fusion is applied to the individual reference images (later images) before determining the information on the progression of the medical constitution of the current patient based on the individual reference images, wherein the information describes the predicted progression at the future time.

39. The method according to the preceding example, wherein the statistical probability and in particular a statistical distribution of pathological parts within the anatomical structure of the current patient at the future time is determined based on the plurality of individual reference images (later images).

40. The method according to one of the preceding examples, wherein information on pathological parts of the anatomical structure is included in the individual reference images and describes information on geometry, preferably size, shape, volume, and/or position of the pathological parts.

41. The method according to one of the preceding examples, wherein the statistical probability is described by a distribution reflecting the structure of the pathological parts based on combination, in particular superposition of the individual reference images (of different patients).

42. The method according to one of the examples 1 to 28, wherein information on the progression is determined by combing a plurality of reference images having same status of progression respectively to one combined image reflecting statistical distribution of pathological structure at a particular status of progression.

43. The method according to one of the examples 1 to 28, wherein such combined images are determined for a plurality of times.

44. The method according to one of the examples 1 to 28, wherein time difference data is acquired defining the progression time difference between present time and future time for which the progression is to be predicted.

45. The method according to one of the examples 1 to 28, wherein that one of the combined images is identified which is most similar to the current image.

46. The method according to one of the examples 1 to 28, wherein that one of the combined images is selected the progression status of which has a time difference to the identified image identical to the progression time, the selected one reflecting the statistical probability.

47. The method wherein a determination of the similarity in examples 29 to 46 is performed in the same manner as described in one of the examples 1 to 28 in particular by using elastic fusion.

48. The method according to one of the preceding examples, wherein information on the progression of the medical constitution of the current patient, particularly the statistical probability of at least one progression scenario of the medical constitution of the current patient is provided, particularly displayed to a person.

49. The method according to one of the preceding examples, wherein treatment data is acquired describing a plurality of potential treatments for the determined progression of the medical constitution of the current patient, particularly the statistical probability of at least one progression scenario of the medical constitution of the current patient.

50. The method according to one of the preceding examples, wherein treatment criteria data is acquired and at least one treatment is selected based on treatment criteria data, and the at least one selected treatment is provided, particularly displayed to a person.

51. The method according to one of the preceding examples, wherein a treatment decision is made based on criteria data acquired for selecting at least one appropriate treatment, preferably the most appropriate treatment.

53. The method according to one of the preceding examples, wherein the medical treatment is a radiation therapy treatment.

54. The method according to one of the preceding examples, wherein the progression analyzed is the development of metastasis, particularly of metastasis in the brain.

54. The method according to one of the preceding examples, wherein the order and/or location at which metastasis for the current patient is compared to the order and/or location of metastasis for the at least one reference patient.

55. The method according to one of the preceding examples, wherein cloud technology is used for acquiring patient data.

56. The method according to one of the preceding examples, wherein at least one cloud based server is used for determining information on the progression of the medical constitution of the current patient.

57. The program which, when running on a computer or when loaded onto a computer, causes the computer to perform the method steps of the method according to one of the preceding examples and/or to a program storage medium on which the program is stored and/or to a computer on which the program is running or into the memory of which the program is loaded and/or to a signal wave, in particular a digital signal wave, carrying information which represents the program.

58. The computer according to the preceding example, wherein the computer comprises a cloud server.

The invention claimed is:

1. A processor-implemented method performed by a computer for planning a medical treatment, the method comprising:
   receiving, at a processor of the computer, reference patient image data describing medical information on at least two reference patients including information on a progression of a medical constitution of the at least two reference patients;
   superimposing, by the processor, reference images of the at least two reference patients showing same stages of the progression of the medical constitution, respectively, to create combined reference patient image data reflecting a statistical distribution of a pathological structure at at least two successive reference stages of the progression of the medical constitution, wherein a first elastic fusion transformation is used to adapt anatomical data of the at least two reference patients relative to each other;
   receiving, at the processor, current patient image data describing medical information on a current patient including information on a medical constitution of the current patient and reflecting a pathological structure at a particular stage of a progression of the medical constitution of the current patient, the particular stage of the progression of the medical constitution of the current patient corresponding to a particular reference stage between the at least two successive reference stages of the progression of the medical constitution in the at least two reference patients;
   determining a transformation matrix comprising a second elastic fusion transformation used to adapt a combined reference patient image reflecting an earlier reference stage of progression of the medical constitution in the at least two reference patients to a current image reflecting the particular stage of a progression of the medical constitution of the current patient;
   obtaining a predicted progression of the medical constitution of the current patient by applying the transformation matrix to a combined reference image reflecting a later reference stage of progression of the medical constitution in the at least two reference patients occurring after the particular reference stage of the progression of the medical constitution in the at least two reference patients; and
   sending, from the processor, data representative of the predicted progression of the medical constitution of the current patient, the data representative of the predicted progression of the current patient comprising information on a statistical distribution of geometry and/or position of pathological parts within an anatomical structure of the current patient data at a future time.

2. The method according to claim 1, wherein receiving the reference patient image data comprises receiving reference patient image data of at least one reference patient at different times, generated by carrying out at least two examinations of at least one reference patient at different times, and wherein information on the progression of the medical constitution of the at least one reference patient includes a sequence of medical constitution data comprising a sequence of image data of the at least one reference patient.

3. The method according to claim 1, wherein receiving the current patient data comprises receiving patient data of the current patient at least once by carrying out at least one examination of the current patient, which is of the same type of examination as carried out on a reference patient.

4. The method according to claim 1, wherein the receiving reference patient image data comprises:
   acquiring criteria data describing criteria for comparing pool patient data to current patient data, the pool patient data comprising patient data of a plurality of patients, and the criteria data comprising at least one of generic medical data including age, gender, blood group, tumor grades, ICD-9 classification, Simpson grade, oxygenation of tumor, degree of metastasis of tumor, blood count value tumor indicator value like PA value, wherein criteria data describes a requirement according to which medical information at the time of a particular status of progression of the medical constitution is included in the pool patient data of a patient;
   determining the reference patient image data of a plurality of reference patients, by selecting a set of the pool patient data with the criteria data as a criterion, wherein determining the reference patient image data comprises determining similarity of current patient data and pool patient data by considering similarity of the status of progression of the medical constitution of the current patient and a pool patient.

5. The method according to claim 1, wherein elastic fusion transformation is used to cross-reference current patient data with pool patient data.

6. The method according to claim 1, wherein image data subtraction, is used to determine a degree of similarity of the data that is transformed by said elastic fusion transformation.

7. The method according to claim 1, wherein determining information on the progression of the medical constitution of the current patient comprises determining a statistical probability of at least one progression scenario, of the medical constitution of the current patient based on the reference patient data and the current patient data.

8. The method according to claim 1, wherein reference images are selected by applying the said criteria data as a criterion, so as to determine the information on the progression of the medical constitution of the current patient which are linked to the same or at least most similar status of progression as the status of progression linked to the current image and/or those ones of the reference images are used for performing the elastic fusion transformation.

9. The method according to claim 1, wherein information on pathological parts of the anatomical structure is included in individual reference images and describes information on geometry, preferably size, shape, volume, and/or position of the pathological parts.

10. The method according to claim 1, wherein information on the progression of the medical constitution of the current patient is displayed to a person.

11. The method according to claim 1, wherein treatment data is acquired describing a plurality of potential treatments for the determined progression of the medical constitution of the current patient wherein at least one treatment is selected based on treatment criteria data acquired for selecting at least one appropriate treatment, and the at least one selected treatment is displayed to a person.

12. The method according to claim 1, wherein the medical treatment is a radiation therapy treatment, wherein the order and/or location at which metastasis for the current patient is compared to the order and/or location of metastasis for the at least one reference patient.

13. A non-transitory computer-readable storage device storing a computer program which, when running on a computer or when loaded onto a computer, causes the computer to perform a method for planning a medical treatment comprising:

receiving, at a processor of the computer, reference patient image data describing medical information on at least two reference patients including information on progression of a medical constitution of the at least two reference patients;

superimposing, by the processor, reference images of the at least two reference patients showing same stage of the progression of the medical constitution, respectively, to create combined reference patient image data reflecting a statistical distribution of a pathological structure at at least two successive reference stages of the progression of the medical constitution, wherein a first elastic fusion transformation is used to adapt anatomical data of the at least two reference patients relative to each other;

receiving, at the processor, current patient image data describing medical information on a current patient including information on a medical constitution of the current patient and reflecting a pathological structure at a particular stage of a progression of the medical constitution of the current patient, the particular stage of the progression of the medical constitution of the current patient corresponding to a particular reference stage between the at least two successive reference stages of the progression of the medical constitution in the at least two reference patients;

determining a transformation matrix comprising a second elastic fusion transformation used to adapt a combined reference patient image reflecting an earlier reference stage of progression of the medical constitution in the at least two reference patients to a current image reflecting the particular stage of a progression of the medical constitution of the current patient;

obtaining a predicted progression of the medical constitution of the current patient by applying the transformation matrix to a combined reference image reflecting a later reference stage of progression of progression of the medical constitution in the at least two reference patients occurring after the particular reference stage of the progression of the medical constitution in the at least two reference patients; and sending, from the processor, data representative of the predicted progression of the medical constitution of the current patient, the data as representative of the predicted progression of the current patient comprising information on a statistical distribution of geometry and/or position of pathological parts within an anatomical structure of the current patient data at a future time.

14. The computer according to claim 13, wherein the computer comprises a cloud server.

* * * * *